(12) United States Patent
Biedermann et al.

(10) Patent No.: US 9,468,483 B2
(45) Date of Patent: Oct. 18, 2016

(54) BONE SCREW

(71) Applicant: Biedermann Technologies GmbH & Co. KG, Donaueschingen (DE)

(72) Inventors: Lutz Biedermann, VS-Villingen (DE); Jürgen Harms, Karlsruhe (DE); Ronald W. Lindsey, Houston, TX (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/600,715

(22) Filed: Jan. 20, 2015

(65) Prior Publication Data

US 2015/0320469 A1   Nov. 12, 2015

Related U.S. Application Data

(63) Continuation of application No. 14/021,278, filed on Sep. 9, 2013, now Pat. No. 8,968,372, which is a continuation of application No. 13/367,729, filed on Feb. 7, 2012, now abandoned, which is a continuation of application No. 10/181,182, filed on Jul. 10, 2002, now Pat. No. 8,137,389.

(30) Foreign Application Priority Data

Nov. 10, 2000  (DE) .................................. 100 55 891
Nov. 12, 2001  (WO) ........................ PCT/EP01/13080

(51) Int. Cl.
*A61B 17/04*   (2006.01)
*A61B 17/86*   (2006.01)

(52) U.S. Cl.
CPC ........... *A61B 17/864* (2013.01); *A61B 17/863* (2013.01); *A61B 17/869* (2013.01); *A61B 17/8615* (2013.01); *A61B 17/8635* (2013.01); *A61B 17/8685* (2013.01)

(58) Field of Classification Search
CPC ..................... A61F 2/44; A61F 2/4455–2/448
USPC ......... 606/300–321; 411/411–426, 385, 388, 411/389, 395–397
See application file for complete search history.

(56) References Cited

U.S. PATENT DOCUMENTS

| 10,473 A | 1/1854 | Johnson |
| 945,370 A | 1/1910 | Braddock |

(Continued)

FOREIGN PATENT DOCUMENTS

| DE | 199 49 285 A1 | 5/2001 |
| EP | 0 305 417 B1 | 6/1995 |

(Continued)

OTHER PUBLICATIONS

Boothroyd et al., Product Design for Manufacture and Assembly, 1994, Marcel Dekker, Inc., pp. 64 and 77.

*Primary Examiner* — Matthew Lawson
(74) *Attorney, Agent, or Firm* — Lewis Roca Rothgerber Christie LLP

(57) ABSTRACT

A bone screw is created, with a thread section (1) with a tip (6) at a first end and a head (8) for engaging with a screwdriver at the opposite second end, which serves as traction element to connect shattered or split off parts of bones to one another. So that fusion of the screw with the bones can take place, the thread section (1) is constructed as tubular and its wall has a plurality of recesses.

11 Claims, 3 Drawing Sheets

(56) References Cited

U.S. PATENT DOCUMENTS

| | | |
|---|---|---|
| 1,131,342 A | 3/1915 | Dodds |
| 1,988,813 A | 1/1935 | Seguin |
| 2,993,950 A | 7/1961 | Forman |
| 3,678,925 A | 7/1972 | Fischer et al. |
| 3,716,051 A | 2/1973 | Fischer |
| 3,805,775 A | 4/1974 | Fischer et al. |
| 4,043,239 A | 8/1977 | DeFusco |
| 4,275,263 A | 6/1981 | Chino |
| 4,456,005 A | 6/1984 | Lichty |
| 4,484,570 A | 11/1984 | Sutter et al. |
| 4,708,132 A | 11/1987 | Silvestrini |
| 4,760,843 A | 8/1988 | Fischer et al. |
| 4,964,403 A | 10/1990 | Karas et al. |
| 5,015,247 A | 5/1991 | Michelson |
| 5,019,079 A | 5/1991 | Ross |
| 5,030,052 A | 7/1991 | Anderson et al. |
| 5,129,904 A | 7/1992 | Illi |
| 5,160,225 A | 11/1992 | Chern |
| 5,209,753 A | 5/1993 | Biedermann et al. |
| 5,217,462 A | 6/1993 | Asnis et al. |
| 5,366,374 A | 11/1994 | Vlassis |
| 5,458,638 A | 10/1995 | Kuslich et al. |
| 5,489,308 A | 2/1996 | Kuslich et al. |
| 5,547,323 A | 8/1996 | Fang |
| 5,658,285 A | 8/1997 | Marnay et al. |
| 5,672,176 A | 9/1997 | Biedermann et al. |
| 5,683,391 A | 11/1997 | Boyd |
| 5,735,898 A | 4/1998 | Brånemark |
| 5,743,912 A | 4/1998 | Lahille et al. |
| 5,797,914 A | 8/1998 | Leibinger |
| 5,800,553 A | 9/1998 | Albrektsson et al. |
| 5,827,285 A * | 10/1998 | Bramlet ............. A61B 17/68 411/166 |
| 5,849,004 A | 12/1998 | Bramlet |
| 5,860,973 A | 1/1999 | Michelson |
| 5,868,749 A | 2/1999 | Reed |
| 5,906,616 A | 5/1999 | Pavlov et al. |
| 5,964,761 A | 10/1999 | Kambin |
| 5,964,767 A | 10/1999 | Tapia et al. |
| 5,968,047 A | 10/1999 | Reed |
| 5,968,098 A * | 10/1999 | Winslow ............. A61B 17/025 606/248 |
| 5,972,031 A | 10/1999 | Biedermann et al. |
| 6,022,352 A | 2/2000 | Vandewalle |
| 6,048,343 A | 4/2000 | Mathis et al. |
| 6,053,916 A | 4/2000 | Moore |
| 6,059,785 A | 5/2000 | Schavan et al. |
| 6,086,589 A | 7/2000 | Kuslich et al. |
| 6,120,502 A | 9/2000 | Michelson |
| 6,187,005 B1 | 2/2001 | Brace et al. |
| 6,214,012 B1 | 4/2001 | Karpman et al. |
| 6,299,642 B1 | 10/2001 | Chan |
| 6,319,255 B1 | 11/2001 | Grundei et al. |
| 6,391,058 B1 | 5/2002 | Kuslich et al. |
| 6,447,546 B1 * | 9/2002 | Bramlet ............. A61F 2/446 623/17.11 |
| 6,454,810 B1 | 9/2002 | Lob |
| 6,517,542 B1 * | 2/2003 | Papay ............. A61B 17/0401 606/232 |
| 6,558,388 B1 | 5/2003 | Bartsch et al. |
| 6,565,572 B2 | 5/2003 | Chappius |
| 6,605,089 B1 | 8/2003 | Michelson |
| 8,357,186 B2 * | 1/2013 | Hadi ............. A61B 17/683 606/246 |
| 2001/0007072 A1 | 7/2001 | Steiner et al. |
| 2001/0021852 A1 | 9/2001 | Chappius |
| 2003/0033019 A1 | 2/2003 | Lob |

FOREIGN PATENT DOCUMENTS

| | | |
|---|---|---|
| EP | 0 682 917 A1 | 11/1995 |
| EP | 0 790 038 A1 | 8/1997 |
| JP | 7-51292 | 2/1995 |
| MU | 7900887-9 U | 7/2000 |
| WO | WO 96/28118 | 9/1996 |
| WO | WO 97/37603 | 10/1997 |
| WO | WO 00/10473 | 3/2000 |
| WO | WO 02/11630 A1 | 2/2002 |

* cited by examiner

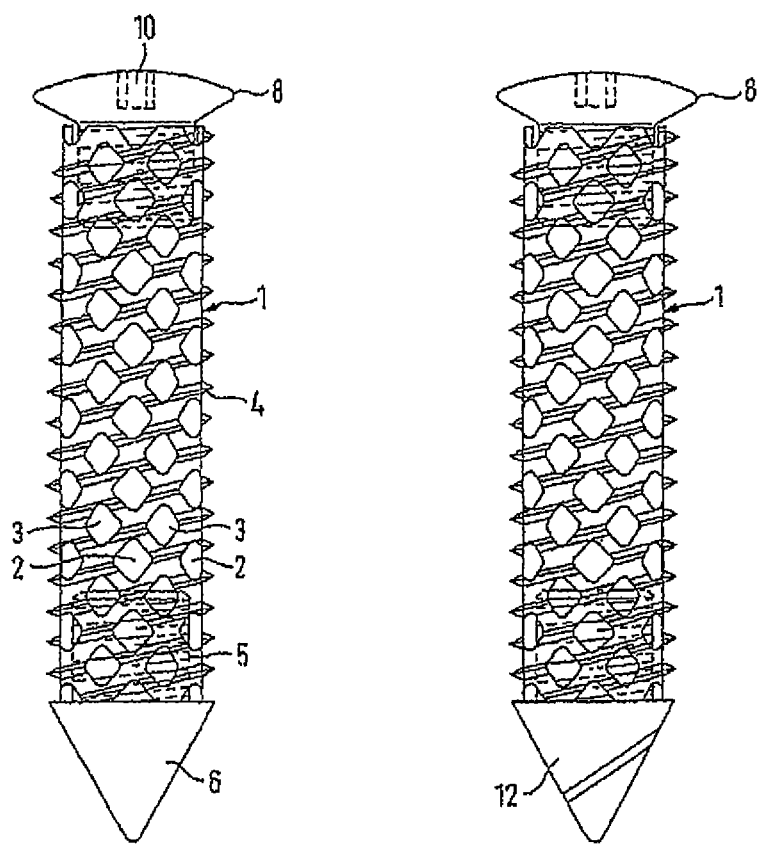

BONE SCREW

CROSS-REFERENCE TO RELATED APPLICATIONS

This application is a continuation of U.S. patent application Ser. No. 14/021,278, filed Sep. 9, 2013, which is a continuation of U.S. patent application Ser. No. 13/367,729, filed Feb. 7, 2012, which is a continuation of U.S. patent application Ser. No. 10/181,182 filed Jul. 10, 2002, now U.S. Pat. No. 8,137,389, which claims the priority benefit of PCT Patent Application No. EP01/13080 filed Nov. 12, 2001, and which claims the priority benefit of German Patent Application No. 100 55 891.7 filed Nov. 10, 2000, the disclosures of which are incorporated herein by reference.

BACKGROUND OF THE INVENTION

The invention relates to a bone screw with a thread section, a tip on a first end and a head for engaging with a screwdriver at the opposite second end.

From EP-A-0 682 917 a hollow cylindrical pin is known, which has an outer bone thread, beginning at a distance from its tip, and also recesses in its outer casing to enable bone integration. The device is constructed in such a way that screwing in is possible only into a drilled hole, which has to be made beforehand.

From WO 97/37603 a bone screw is known, the shank of which has a plurality of perforations, made by drilling, for growing in.

From U.S. Pat. No. 6,048,343 a bone screw system with a chamfered bone screw is known.

SUMMARY OF THE INVENTION

The object of the invention is to improve a bone screw of the kind initially described.

This object is achieved by a bone screw in which the tubular thread section has a bone thread on its outer wall and at least at one end an inner thread section for screwing in the head or tip. This produces great variability, as various heads or tips can be screwed in.

According to a further development the inner thread extends over the entire length of the thread section. In this way the advantage is achieved that the thread section can be shortened in situ to any desired length, so here too variability is increased.

According to another solution the bone screw is characterised in that the tubular thread section has a bone thread on its outer wall and the tip is constructed as a self-cutting tip. This does away with the necessity of first making a bore to accommodate the screw. A further solution is characterised in that the tubular thread section has a bone thread on its outer wall and the head and/or the tip are so dimensioned that they can be inserted to fit snugly into the ends of the thread section. Here again the variability of ways of insertion is increased if the thread section can be shortened in situ to a desired length and then head or tip of the desired kind can be inserted.

Further developments of the invention are characterised in the subordinate claims.

BRIEF DESCRIPTION OF THE DRAWINGS

Further features and advantages of the invention emerge from the description of embodiment examples using the figures.

FIG. 2 shows a compiled screw of a first embodiment.
FIG. 3 shows a compiled screw of a second embodiment.

DETAILED DESCRIPTION OF THE INVENTION

Figure 1:
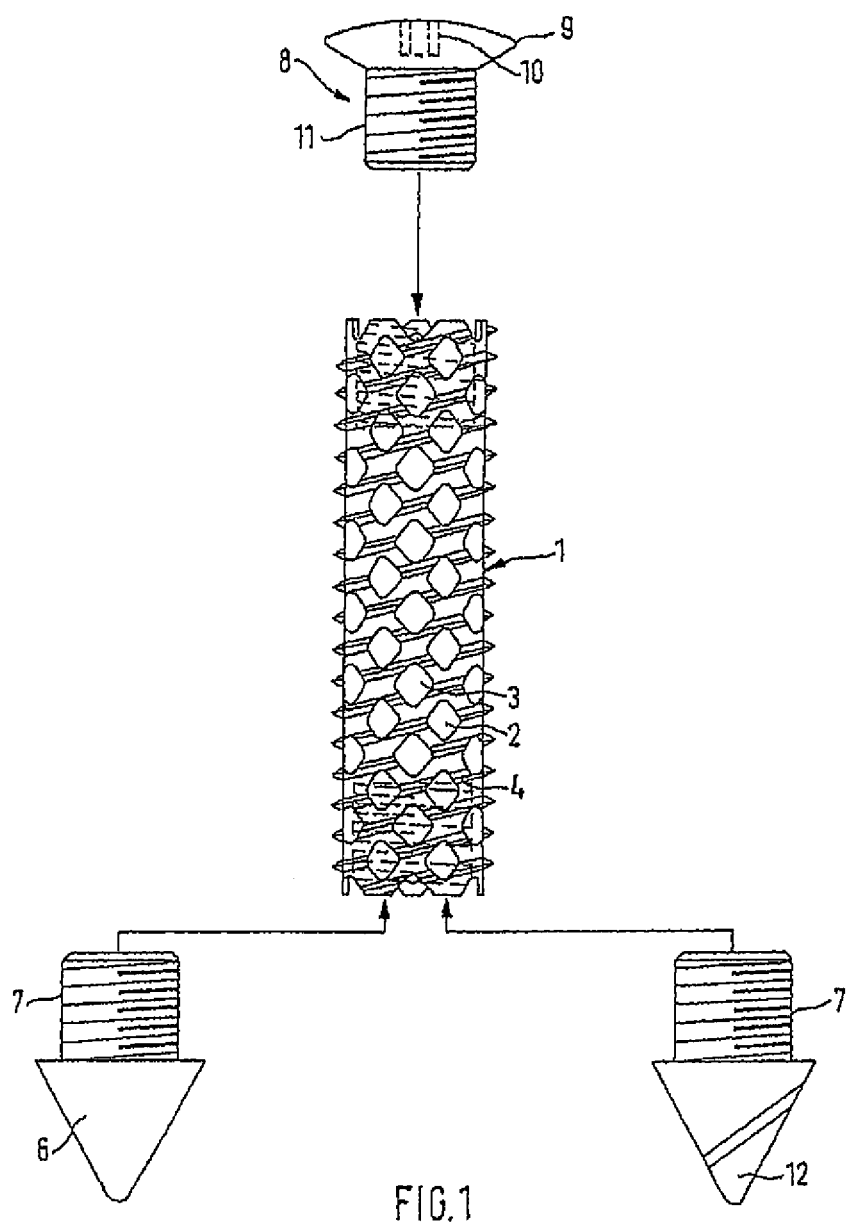
FIG. 1 shows an exploded illustration.

As can best be seen from FIG. 1, the bone screw has a tubular thread section 1. This has in its wall a multiplicity of recesses 2, which in the embodiment example shown are constructed as lozenge-shaped. Alignment of the lozenges therein takes place in such a way that in each case one symmetrical axis extends parallel to the symmetrical axis of the tube. A first set of recesses 2 is offset from one another in the circumferential direction. Adjacent, seen in the axial direction, there follows a further set of recesses 3, which seen in the circumferential direction are at the same distance, but are so arranged that in each case, seen in the axial direction, an orifice of the second set 3 lies between two orifices of the preceding set 2. The pattern continues over the entire surface. Although the orifices are preferably constructed as lozenge-shaped, according to other embodiment examples other forms of orifice, in particular round orifices, can be provided.

Figure 4:
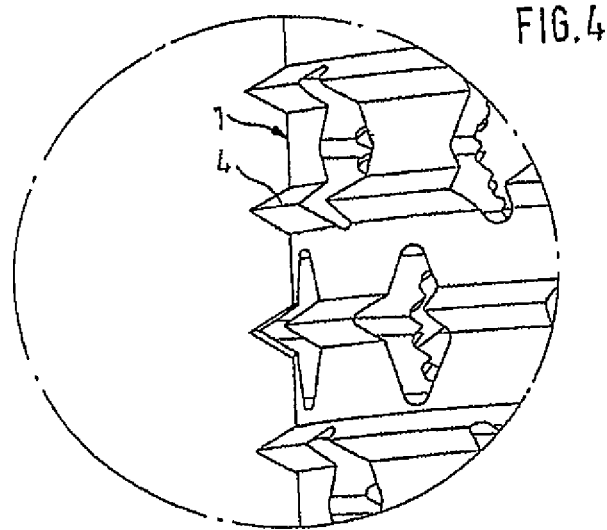
FIG. 4 shows a detail from FIG. 1 in enlarged scale.
Figure 5:
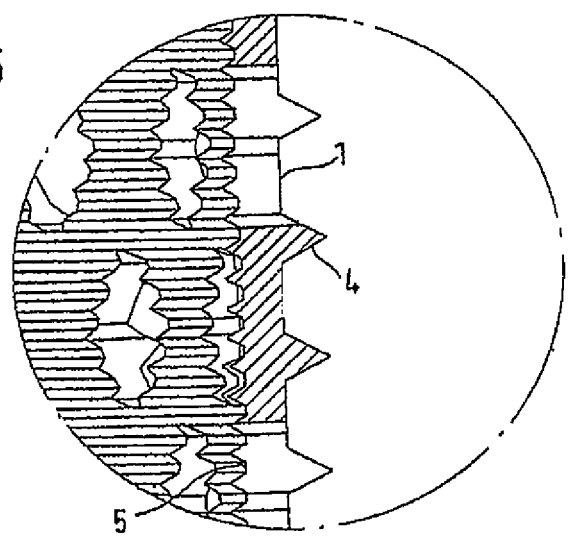
FIG. 5 shows a detail from FIG. 1 in section in enlarged scale.

On the outer wall a so-called bone thread 4 is provided, which in shape corresponds to the normal bone screws. The bone thread is shown in detail in FIG. 4.

The bone screw further comprises a tip 6 attached to one end of the tube. The tip comprises the actual tip part and a shank 7. In the embodiment example shown the shank 7 has a metric outer thread. The tubular thread section 1 has on its inner wall a corresponding metric inner thread and the tip and the tube are rigidly connected to one another by screwing in the tip in the way which can be seen in FIG. 2. The two metric threads are therein constructed as left threads against the right thread inclination of the bone thread 4.

The bone screw further comprises a head 8, which, as can best be seen from FIG. 1, has the actual head part 9 with a slit or an inner hexagon 10 and a thread shank 11. The tube forming the thread section 1 has on its associated end a metric inner thread which matches the thread of the thread shank 11. The two cooperating threads of the thread shank 11 and the inner thread are also preferably constructed as left threads. The head 8 is rigidly screwed into the thread section 1 in the way shown in FIG. 2.

The embodiment shown in FIG. 3 differs from the first described embodiment in that the tip 12 is constructed as a self-cutting tip. In this embodiment and also in the first embodiment the tips are rounded off in each case in the way shown in the figures.

In the above-described embodiments the tip and the head are screwed in. The metric inner thread extends in each case over the two ends in such a way that head and tip can be screwed in.

According to a preferred embodiment the inner thread extends over the entire length of the thread section. This has the advantage that the tube can be cut to any length, so screws of desired length can be produced, so storage can be considerably reduced.

According to an alternative embodiment the inner wall of the thread section 1 and the respective shanks 7 and 11 are constructed without the respective threads and defined in their measurements in such a way that tip and head are rigidly connected to fit snugly to the thread section 1.

Alternatively a thread can be provided at one end and the associated element, in other words tip or head, can have a corresponding thread and be able to be screwed in, so at this end cutting the tube to a predetermined length remains possible, and the other element, in other words head or tip, can be attached to fit snugly.

The parts forming the bone screw are preferably made of titanium.

The possibility of screwing in tip and head also creates the advantage that bone material or some other growth-promoting material can be filled into the cavity of the thus formed screw, thus greatly accelerating the healing process.

What is claimed is:

1. A bone screw comprising:
   a monolithic tubular body with a first end and a second end, the tubular body having a wall with a plurality of recesses, the wall further comprising an exterior bone thread extending over an entire length of the tubular body from the first end to the second end and an interior tubular surface extending inwardly from each of the first and second ends;
   a head configured to engage with a driver and configured to directly connect to the interior tubular surface at the first end of the tubular body; and
   a tip configured to directly connect to the interior tubular surface at the second end of the tubular body;
   wherein a cross-sectional profile of the external bone thread is constant along the entire length of the tubular body from the first end to the second end.

2. The bone screw according to claim 1, wherein the tip comprises a self-cutting tip.

3. The bone screw according to claim 1, wherein the interior tubular surface comprises an inner thread section comprising a metric thread.

4. The bone screw according to claim 3, wherein the tip comprises a self-cutting tip.

5. The bone screw according to claim 1, wherein the interior tubular surface extends over the entire length of the tubular body from the first end to the second end.

6. A bone screw according to claim 5, wherein the interior tubular surface comprises an inner thread extending over the entire length of the tubular body from the first end to the second.

7. A bone screw comprising a monolithic tubular body with two ends, a tip at a first end, and a head for engaging with a screwdriver at an opposite second end, the tubular body having a wall with a plurality of recesses, the wall further comprising an exterior bone thread extending over an entire length of the tubular body from the first end to the second end and an interior tubular surface having an inner thread extending over the entire length of the tubular body from the first end to the second end, wherein the tip is configured to directly connect to the inner thread.

8. A bone screw according to claim 7, wherein the tip comprises a self-cutting tip.

9. A method of attaching a bone screw to a bone, the bone screw comprising a monolithic tubular body with a first end and a second end, the tubular body having a wall with a plurality of recesses, the wall further comprising an exterior bone thread extending over an entire length of the tubular body from the first end to the second end and an interior tubular surface extending inwardly from each of the first and second ends, a head configured to engage with a driver and configured to directly connect to the interior tubular surface at the first end of the tubular body; and a tip configured to directly connect to the interior tubular surface at the second end of the tubular body, wherein an outer diameter of the external bone thread is constant over the entire length of the tubular body from the first end to the second end, the method comprising:

cutting the tubular body to a length;
   attaching the tip at the first end of the tubular body;
   attaching the head at the second end of the tubular body; and
   screwing the tubular body into a bone.

10. The method according to claim 9, wherein the step of attaching the tip at the first end of the tubular body occurs before cutting the tubular body to a length.

11. The method according to claim 9, wherein the step of attaching the head at the second end of the tubular body occurs before cutting the tubular body to a length.

* * * * *